(12) United States Patent
Orr et al.

(10) Patent No.: US 11,523,773 B2
(45) Date of Patent: Dec. 13, 2022

(54) BIOFEEDBACK FOR THERAPY IN VIRTUAL AND AUGMENTED REALITY

(71) Applicant: XR Health IL LTD, Tel Aviv (IL)

(72) Inventors: Eran Orr, Brookline, MA (US); Omer Weissberger, Even-Yehuda (IL)

(73) Assignee: XR Health IL LTD, Tel Aviv (IL)

( * ) Notice: Subject to any disclaimer, the term of this patent is extended or adjusted under 35 U.S.C. 154(b) by 479 days.

(21) Appl. No.: 16/793,648

(22) Filed: Feb. 18, 2020

(65) Prior Publication Data

US 2020/0178885 A1    Jun. 11, 2020

Related U.S. Application Data

(63) Continuation of application No. PCT/US2018/000348, filed on Aug. 20, 2018.

(Continued)

(51) Int. Cl.
*A61B 5/00*    (2006.01)
*G16H 20/30*   (2018.01)
(Continued)

(52) U.S. Cl.
CPC ............ *A61B 5/486* (2013.01); *A61B 5/0205* (2013.01); *G06F 3/015* (2013.01); *G09B 5/02* (2013.01); *G16H 10/60* (2018.01); *G16H 20/30* (2018.01); *A61B 3/112* (2013.01); *A61B 5/021* (2013.01); *A61B 5/024* (2013.01); *A61B 5/0816* (2013.01); *A61B 5/369* (2021.01); *A61B 5/389* (2021.01);
(Continued)

(58) Field of Classification Search
CPC ...... A61B 5/486; A61B 5/0205; G16H 10/60; G16H 20/30; G06F 3/015; G09B 5/02
See application file for complete search history.

(56) References Cited

U.S. PATENT DOCUMENTS

2012/0259652 A1   10/2012  Mallon et al.
2016/0005320 A1   1/2016   deCharms et al.
(Continued)

FOREIGN PATENT DOCUMENTS

WO    WO-2019/036051 A1    2/2019

OTHER PUBLICATIONS

International Search Report and Written Opinion for International Application No. PCT/US2018/00348 dated Nov. 28, 2018.

*Primary Examiner* — Curtis B Odom
(74) *Attorney, Agent, or Firm* — Erik A. Huestis; Foley Hoag LLP

(57) ABSTRACT

Adjustment of training protocols in virtual reality (VR) or augmented reality (AR) environments based on biofeedback are provided. In various embodiments, motion data is collected for a user while the user performs a training protocol in a virtual environment. A biometric measurement is collected for the user while the user performs the training protocol. The motion data and the biometric measurement are provided to a learning system at a remote server. The learning system determines an adjustment to the training protocol based on the motion data and the biometric measurement. The adjustment is provided by the learning system and is applied to the training protocol. In various embodiments, the adjustment, the motion data, and/or the biometric measurement may be logged in an electronic health record.

20 Claims, 4 Drawing Sheets

Related U.S. Application Data

(60) Provisional application No. 62/547,321, filed on Aug. 18, 2017.

(51) Int. Cl.
| | | |
|---|---|---|
| *G16H 10/60* | (2018.01) | |
| *A61B 5/0205* | (2006.01) | |
| *G06F 3/01* | (2006.01) | |
| *G09B 5/02* | (2006.01) | |
| *A61B 3/11* | (2006.01) | |
| *A61B 5/021* | (2006.01) | |
| *A61B 5/024* | (2006.01) | |
| *A61B 5/08* | (2006.01) | |
| *G09B 19/00* | (2006.01) | |
| *A61B 5/369* | (2021.01) | |
| *A61B 5/389* | (2021.01) | |

(52) U.S. Cl.
CPC ......... *A61B 5/4266* (2013.01); *A61B 2505/09* (2013.01); *G09B 19/003* (2013.01)

(56) References Cited

U.S. PATENT DOCUMENTS

| | | |
|---|---|---|
| 2016/0077547 A1 | 3/2016 | Aimone et al. |
| 2017/0004260 A1* | 1/2017 | Moturu ................. G16H 10/60 |
| 2017/0188976 A1 | 7/2017 | Kalra et al. |
| 2017/0333666 A1 | 11/2017 | Goldberg et al. |

* cited by examiner

BIOFEEDBACK FOR THERAPY IN VIRTUAL AND AUGMENTED REALITY

CROSS-REFERENCE TO RELATED APPLICATIONS

This application is a continuation of International Application No. PCT/US2018/0000348, filed Aug. 20, 2018, which claims the benefit of U.S. Provisional Application No. 62/547,321 filed Aug. 18, 2017, each of which is hereby incorporated by reference herein in its entirety.

BACKGROUND

Embodiments of the present disclosure relate to therapy using virtual or augmented reality, and more specifically, to adjusting training protocols in virtual reality (VR) or augmented reality (AR) environments based on biofeedback.

BRIEF SUMMARY

According to embodiments of the present disclosure, systems for, methods of, and computer program products for adjusting training protocols in virtual reality (VR) or augmented reality (AR) environments based on biofeedback are provided. In various embodiments, a virtual environment is provided to a user. Motion data is collected for a user while the user performs a training protocol. A biometric measurement is collected for the user while the user performs the training protocol. The motion data and the biometric measurement are provided to a learning system at a remote server. An adjustment is determined at the remote server based on the motion data and the biometric measurement. An adjustment is provided by the learning system and applied to the training protocol.

According to other embodiments of the present disclosure, systems for, methods of, and computer program products for adjusting training protocols in virtual reality (VR) or augmented reality (AR) environments based on biofeedback are provided. In various embodiments, a virtual environment is provided to a user. A biometric measurement is collected for the user while the user performs a cognitive training protocol. The biometric measurement is provided to a learning system at a remote server. An adjustment is determined at the remote server based on the biometric measurement. The adjustment is provided by the learning system and applied to the training protocol.

In various embodiments, the biometric measurement is selected from: heart rate, blood pressure, breathing rate, electrical activity of the muscles, electrical activity of the brain, pupil dilation, and perspiration. In various embodiments, the training protocol is received from a healthcare record server. In various embodiments, the healthcare record server has a database for storing electronic health records. In various embodiments, an electronic health record of the user may be accessed to retrieve one or more parameters related to the training protocol. In various embodiments, the motion data and the biometric measurement are logged in the electronic health record. In various embodiments, the adjustment is logged in the electronic health record.

In various embodiments, whether the biometric measurement is above a threshold is determined. When the biometric measurement is above the threshold, an additional adjustment to the training protocol is determined. The additional adjustment is applied to the training protocol until the biometric measurement is below the threshold. In various embodiments, the threshold is a target heart rate. In various embodiments, whether the biometric measurement is below a bottom threshold is determined. In various embodiments, an additional adjustment to the training protocol is determined when the biometric measurement is below the bottom threshold. The additional adjustment is applied to the training protocol until the biometric measurement is above the bottom threshold.

According to embodiments of the present disclosure, methods of treatment for adjusting training protocols in virtual reality (VR) or augmented reality (AR) environments based on biofeedback are provided. In various embodiments, a treatment plan including a predetermined rehabilitation training protocol is received from a first remote server. A virtual environment is provided to a user. Motion data is collected for the user while the user performs the rehabilitation training protocol. A biometric measurement is collected for the user while the user performs the rehabilitation training protocol. The motion data and the biometric measurement are provided to a learning system at a second remote server. An adjustment is determined at the second remote server based on the motion data and the biometric measurement. An adjustment is provided by the learning system and applied to the rehabilitation training protocol.

According to other embodiments of the present disclosure, methods of treatment for adjusting training protocols in virtual reality (VR) or augmented reality (AR) environments based on biofeedback are provided. In various embodiments, a treatment plan including a predetermined cognitive training protocol is received from a first remote server. A virtual environment is provided to the user. A biometric measurement is collected for the user while the user performs a cognitive training protocol. The biometric measurement is provided to a learning system at a second remote server. An adjustment is determined at the second remote server based on the biometric measurement. The adjustment is provided by the learning system and applied to the cognitive training protocol.

DETAILED DESCRIPTION

Figure 1:
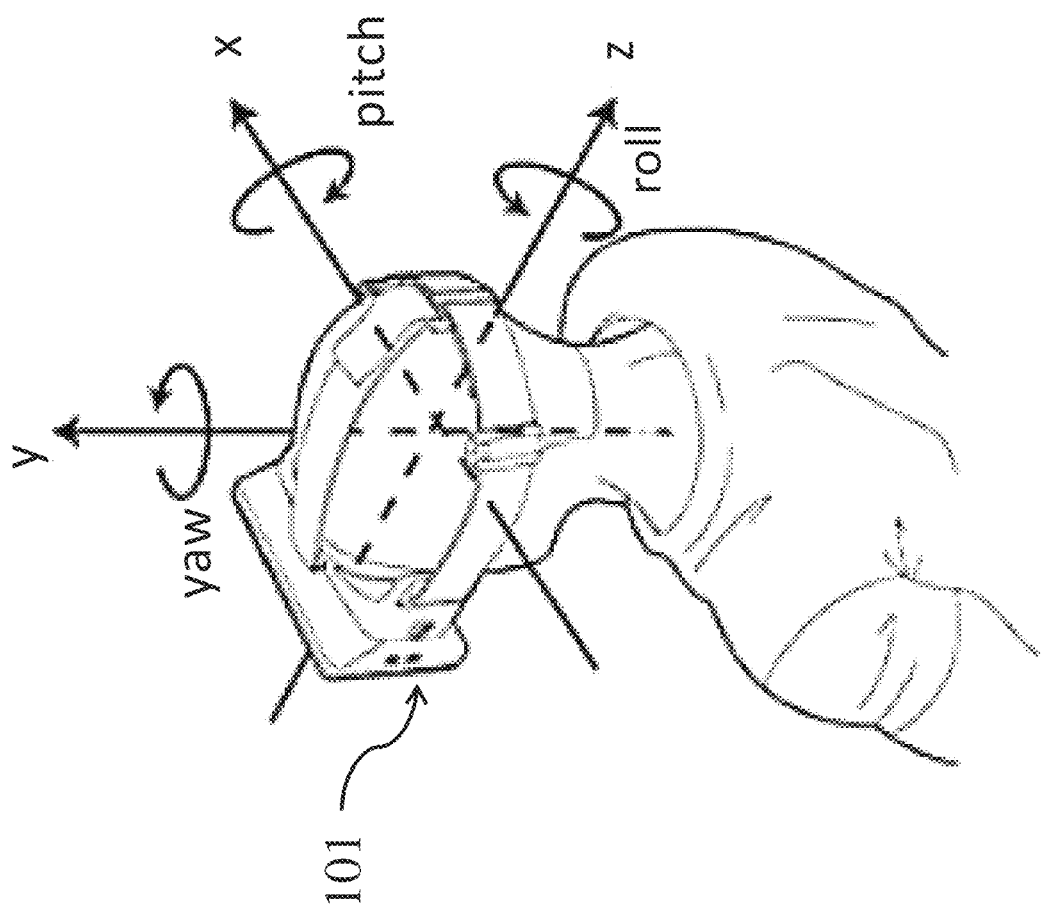
FIG. 1 illustrates an exemplary virtual reality headset according to embodiments of the present disclosure.

Physical therapy attempts to address the illnesses or injuries that limit a person's abilities to move and perform functional activities in their daily lives. Physical therapy may be prescribed to address a variety of pain and mobility issues across various regions of the body. In general, a program of physical therapy is based on an individual's history and the results of a physical examination to arrive at a diagnosis. A given physical therapy program may integrate assistance with specific exercises, manual therapy and manipulation, mechanical devices such as traction, education, physical agents such as heat, cold, electricity, sound waves, radiation, assistive devices, prostheses, orthoses and other interventions. Physical therapy may also be prescribed as a preventative measure to prevent the loss of mobility before it occurs by developing fitness and wellness-oriented programs for healthier and more active lifestyles. This may include providing therapeutic treatment where movement and function are threatened by aging, injury, disease or environmental factors.

As an example, individuals suffer from neck pain or need to perform neck exercises for various reasons. For example, people who have been involved in a motor vehicle accident or have suffered an injury while playing contact sports are prone to develop a whiplash associated disorder (WAD), a condition resulting from cervical acceleration-deceleration (CAD). It will be appreciated that this is just one of many potential injuries that may result in neck injury or pain necessitating rehabilitation.

The majority of people who suffer from non-specific neck pain (NSNP) may have experienced symptoms associated with WAD or have an undiagnosed cervical herniated disc. For this population, the recommended treatment regimen often includes a variety of exercises promoting neck movement and other functional activity training, leading to improved rehabilitation.

Poor adherence to treatment can have negative effects on outcomes and healthcare cost, irrespective of the region of the body affected. Poor treatment adherence is associated with low levels of physical activity at baseline or in previous weeks, low in-treatment adherence with exercise, low self-efficacy, depression, anxiety, helplessness, poor social support/activity, greater perceived number of barriers to exercise and increased pain levels during exercise. Studies have shown that about 14% of physiotherapy patients do not return for follow-up outpatient appointments. Other studies have suggested that overall non-adherence with treatment and exercise performance may be as high as 70%. Patients that suffer from chronic or other long-term conditions (such as those associated with WAD or NSNP) are even less inclined to perform recommended home training.

Adherent patients generally have better treatment outcomes than non-adherent patients. However, although many physical therapy exercises may be carried out in the comfort of one's home, patients cite the monotony of exercises and associated pain as contributing to non-adherence.

Irrespective of adherence, home training has several limitations. With no direct guidance from the clinician, the patient has no immediate feedback to confirm correct performance of required exercises. Lack of such guidance and supervision often leads to even lower adherence. As a result, the pain of an initial sensed condition may persist or even worsen—leading to other required medical interventions that could have been prevented, thus also increasing associated costs of the initial condition.

It will be appreciated that although the above discussion focuses on physical therapy examples, similar compliance issues are present in a variety of individual training exercises, including coordination training, cognitive training, aversion therapy, and other psychological exercises.

Accordingly, there is a need for devices, systems, and methods that facilitate comprehensive performance and compliance with therapy protocols and therapeutic exercise regimens.

According to various embodiments of the present disclosure, various devices, systems, and methods are provided to facilitate therapy and physical or psychological training assisted by virtual or augmented reality environments.

It will be appreciated that a variety of virtual and augmented reality devices are known in the art. For example, various head-mounted displays providing either immersive video or video overlays are provided by various vendors. Some such devices integrate a smart phone within a headset, the smart phone providing computing and wireless communication resources for each virtual or augmented reality application. Some such devices connect via wired or wireless connection to an external computing node such as a personal computer. Yet other devices may include an integrated computing node, providing some or all of the computing and connectivity required for a given application.

Virtual or augmented reality displays may be coupled with a variety of motion sensors in order to track a user's motion within a virtual environment. Such motion tracking may be used to navigate within a virtual environment, to manipulate a user's avatar in the virtual environment, or to interact with other objects in the virtual environment. In some devices that integrate a smartphone, head tracking may be provided by sensors integrated in the smartphone, such as an orientation sensor, gyroscope, accelerometer, or geomagnetic field sensor. Sensors may be integrated in a headset, or may be held by a user, or attached to various body parts to provide detailed information on user positioning.

In various embodiments, the VR/AR system may determine the position of the body part and record the position over time. In various embodiments, as described in more detail above, one or more sensors may be attached to or otherwise associated with a body part to track a three-dimensional position and motion of the body part with six degrees of freedom. In various embodiments, the system may determine a plurality of positions of one or more body parts. The plurality of positions may correspond to points along a three-dimensional path taken by the body part.

In various embodiments, the system may track the position and motion of the head. In various embodiments, the system may utilize sensors in a head-mounted display to determine the position and motion of the head with six degrees of freedom as described below. Head tracking may be implemented in various embodiments where position/motion data provide an indication (sole or additional) of compliance with a rehabilitation protocol. For example, head tracking may be implemented when using a rehabilitation protocol that includes neck exercises.

In various embodiments, for more nuanced exercises, one or more additional sensors may provide position/motion data of various body parts.

In the course of rehabilitation and training, a clinician is generally responsible for adapting exercises according to a patient's abilities and needs, and for supervising and providing corrective feedback to the patient. Clinician guidance is an important part of the overall rehabilitation or training process.

According to various embodiments of the present disclosure, biofeedback is used during various training scenarios performed with AR or VR to provide insights during the training itself. Biofeedback includes the monitoring of body measurements, revealing physiological or psychological data of a subject. This enables changing the training, scenery, or other elements in the VR/AR environment according to the user biofeedback. Those insights allow proper adaptation and modification to a training regimen to tailor it to a patient's needs and abilities.

Biofeedback approaches described herein minimize or eliminate the reliance on subjective impressions of a clinician or patient. In this way, the accurate and responsive performance of exercises is increased.

Using biofeedback during training in AR or VR enables accurate adjustment of the training according to the patient's needs and abilities, as the biofeedback relies on objective, measurable parameters. In particular, biometric data/measurements are collected that reflect the user's physiological or psychological state, indicating functioning of the body systems or cognition during the training itself. In various embodiments, biometric data/measurements may be collected for heart rate (pulse), blood pressure, breathing rate, inhalation and/or exhalation volume, perspiration, eye blinking rate, electrical activity of muscles, electrical activity of the brain or other parts of the central and/or peripheral nervous systems, or any other suitable biometric measurement as is known in the art.

In various embodiments, an electrocardiogram (EKG) may be used to measure heart rate. In various embodiments, an optical sensor may be used to measure heart rate, for example, in a commercially-available wearable heart rate monitor device. In various embodiments, a wearable device may be used to measure blood pressure separately from or in addition to heart rate. In various embodiments, a spirometer may be used to measure inhalation and/or exhalation volume. In various embodiments, a humidity sensor may be used to measure perspiration. In various embodiments, a camera system may be used to measure the blinking rate of one or both eyes. In various embodiments, a camera system may be used to measure pupil dilation. In various embodiments, an electromyogram (EMG) may be used to measure electrical activity of one or more muscles. The EMG may use one or more electrodes to measure electrical signals of the one or more muscles. In various embodiments, an electroencephalogram (EEG) may be used to measure electrical activity of the brain. The EEG may use one or more electrodes to measure electrical signals of the brain. Any of the exemplary devices listed above may be connected (via wired or wireless connection) to the VR/AR systems described herein to thereby provide biometric data/measurements for analysis.

Adjustment based on biometric factors permits tailoring of the training difficulty level for each patient. The training thereby remains safe, while being challenged enough to make the training efficient for rehabilitation or training.

In various embodiments, the physiological factor may be maintained above or below a predetermined threshold. In various embodiments, the predetermined threshold may be a numerical value (e.g., integer or decimal), a binary value, or a Boolean value. For example, a training or rehabilitation protocol may specify that a heart rate is to be maintained above a certain value, e.g., above/below 100 beats per minute. In various embodiments, the physiological factor may be maintained between a lower threshold and an upper threshold. For example, a training or rehabilitation protocol may specify that a heart rate is to be maintained between two values, e.g., between 80 and 100 beats per minute. In another example, a training or rehabilitation protocol may specify that the threshold is met when perspiration is present on the patient/user. In this example, the threshold may be represented as 'True' or 'False'.

In various embodiments, adjustments made based on biometric data/measurements may change the training protocol for a specific patient/user. For example, if the system determines that a heart rate threshold of 100 beats per minute is too high during the training protocol, the system may adjust the threshold to 90 beats per minute. As another example, if the system determines that a heart rate threshold of 100 beats per minute is too low during the training protocol, the system may adjust the threshold to 110 beats per minute. In various embodiments, the predetermined threshold may be a target heart rate. A target heart rate, as is known in the art, during exercise may be 70-75% of the maximum theoretical heart rate of an individual. The maximum theoretical heart rate of an individual may be a function of age and may be affected by other factors, such as, for example, the health of the particular individual. In various embodiments, the maximum theoretical heart rate may be computed by subtracting the individual's age from 225.

Various advantages of the biofeedback techniques described herein will be apparent. In particular, objective values received live from computerized systems monitoring body measurements allowing more accurate adaptation of training for the patient compared to subjective values received from the clinician. A large variety of manipulations is available using VR and AR. Coupled with biofeedback, VR and AR systems may be used to address a range of patient needs in addition to injury and training. For example, the techniques described herein may be used to address and treat a fear response such as with a phobia by changing the experience (scenery, difficulty, interaction) responsive to biofeedback. Training may be adjusted in a tele-rehabilitation setting, or when the clinician is otherwise absent.

In various embodiments, a fear indicator may be computed for a particular individual using the motion and/or biometric measurements as described above. For example, a heart rate of an individual may gradually or suddenly increase when presented a stimulus that causes a fear response. As additional non-limiting examples, an individual may begin perspiring, produce increased EMG or EEG activity, demonstrate increased breathe volume, and/or demonstrate increased breathing rate when presented with a stimulus that causes a fear response.

A discussion of the biological response to fear can be found in The Biology of Fear by Ralph Adolphs, which is hereby incorporated by reference in its entirety. (See Adolphs, Ralph. "*The Biology of Fear.*" Current biology: CB 23.2 (2013): R79-R93. PMC.). In particular, Adolphs describes that "[t]here are many behavioral fear responses that can be used by conspecific observers to infer fear, and several of them have been quantified as behavioral markers of fear by human investigators (cf. Table 2 for a partial list). These include such laboratory measures as freezing (immobility), increased startle, and increased heart rate."

TABLE 2

| of Adolphs: Measures of fear in rodents (top) and humans (bottom) | |
|---|---|
| Behavioral Test | Measure of Anxiety |
| open field exploration | isolated animal avoids bright open areas and prefers secure nest |
| elevated plus-maze | isolated animal avoids open arms of an elevated maze and prefers closed arms |
| social interaction test | animal in a male pair reduces interaction time with the other animal |
| hypophagia | reduced food intake when anxious (e.g., in novel environments) |
| burying behavior | increased burying of food or other objects |
| open field emergence | less emergence into an open space from a secure nest |
| enhanced startle | increased startle to a loud noise, to conditioned or unconditioned fear stimuli |
| Psychophysiology/endocrine | Fear Questionnaires |
| Skin-conductance response (autonomic arousal) | State-Trait Anxiety Inventory |
| Potentiation of auditory startle (measures several emotions) | Beck Anxiety Inventory |
| Facial EMG (measures several emotions) | Fear Survey Schedule |

TABLE 2-continued of Adolphs: Measures of fear in rodents (top) and humans (bottom)

| | |
|---|---|
| Heart rate, respiration (measures several emotions, not specific) | Fear of Negative Evaluation Scale |
| Pupillometry (autonomic arousal) | Social Avoidance/Distress Scale |
| Salivary cortisol (long-duration arousal, stress) | Anxiety Sensitivity Index |
| | Albany Panic and Phobia Q. |
| | Fear Questionnaire |
| | PANAS-X Fear |

Other measures of fear may be utilized such as those described in a paper entitled *The Human Amygdala and the Induction and Experience of Fear* by J S Feinsten, which is hereby incorporated by reference in its entirety. (See Feinstein J S, Adolphs R, Damasio A, Tranel D. *The human amygdala and the induction and experience of fear.* Curr. Biol. 2011;21:34-38.).

In various embodiments, the VR/AR systems of the present invention provide a virtual environment to a user through, e.g., a VR/AR head-mounted display. While in the virtual environment, in various embodiments, the user may receive direction from the VR/AR system to begin a training/rehabilitation protocol. In various embodiments, the training/rehabilitation protocol may be a cognitive training protocol. In various embodiments, the training/rehabilitation protocol may be retrieved from a remote server having a database that stores, e.g.,, electronic health records. In various embodiments, the training/rehabilitation protocol may be previously entered into the electronic health record by a healthcare provider.

In various embodiments, the training protocol may include various parameters such as, for example, type of exercise, number of repetitions, frequency of training/rehabilitation, duration of training/rehabilitation, and/or parameters related to the biometric data/measurements.

In various embodiments, motion data may be collected for the user while the user performs the training/rehabilitation protocol in the VR/AR environment. In various embodiments, one or more biometric measurements may, simultaneously or separately, be collected for the user while the user performs the training protocol. In various embodiments, the motion data and/or biometric measurement(s) may be provided to a learning system. In various embodiments, the learning system may be located at a remote server. In various embodiments, the learning system may be located at the same remote server as the electronic health record or a different remote server.

In various embodiments, the learning system may determine one or more adjustments to the training/rehabilitation protocol based on the motion data and/or the biometric measurement(s). As described in more detail above, the adjustment may be made to the training/rehabilitation protocol to tailor the training/rehabilitation protocol to a specific patient/user. In various embodiments, the learning system may send the VR/AR system the adjustment(s) over a network. In various embodiments, the VR/AR system may apply the adjustment(s) to the training/rehabilitation protocol. In various embodiments, the adjustment(s) may be applied while the patient/user is performing the training/rehabilitation protocol or before the patient/user begins a future round of training/rehabilitation using the VR/AR system. In various embodiments, any of the motion data, biometric measurement(s), and/or the adjustment(s) may be stored in the patient's electronic health record for a healthcare provider to access.

With reference now to FIG. 1, an exemplary virtual reality headset is illustrated according to embodiments of the present disclosure. In various embodiments, system 100 is used to collected data from motion sensors including hand sensors (not pictured), sensors included in headset 101, and additional sensors such as torso sensors or a stereo camera. In some embodiments, data from these sensors is collected at a rate of up to about 150 Hz. As pictured, data may be collected in six degrees of freedom: X—left/right; Y—up/down/ height; Z—foreword/backward; P—pitch; R—roll; Y—yaw. As set out herein, this data may be used to track a user's overall motion and compliance with a predetermined exercise routine. Likewise, headset 101 may position various moving 2D or 3D objects to guide the user through physical training protocols.

Figure 2:
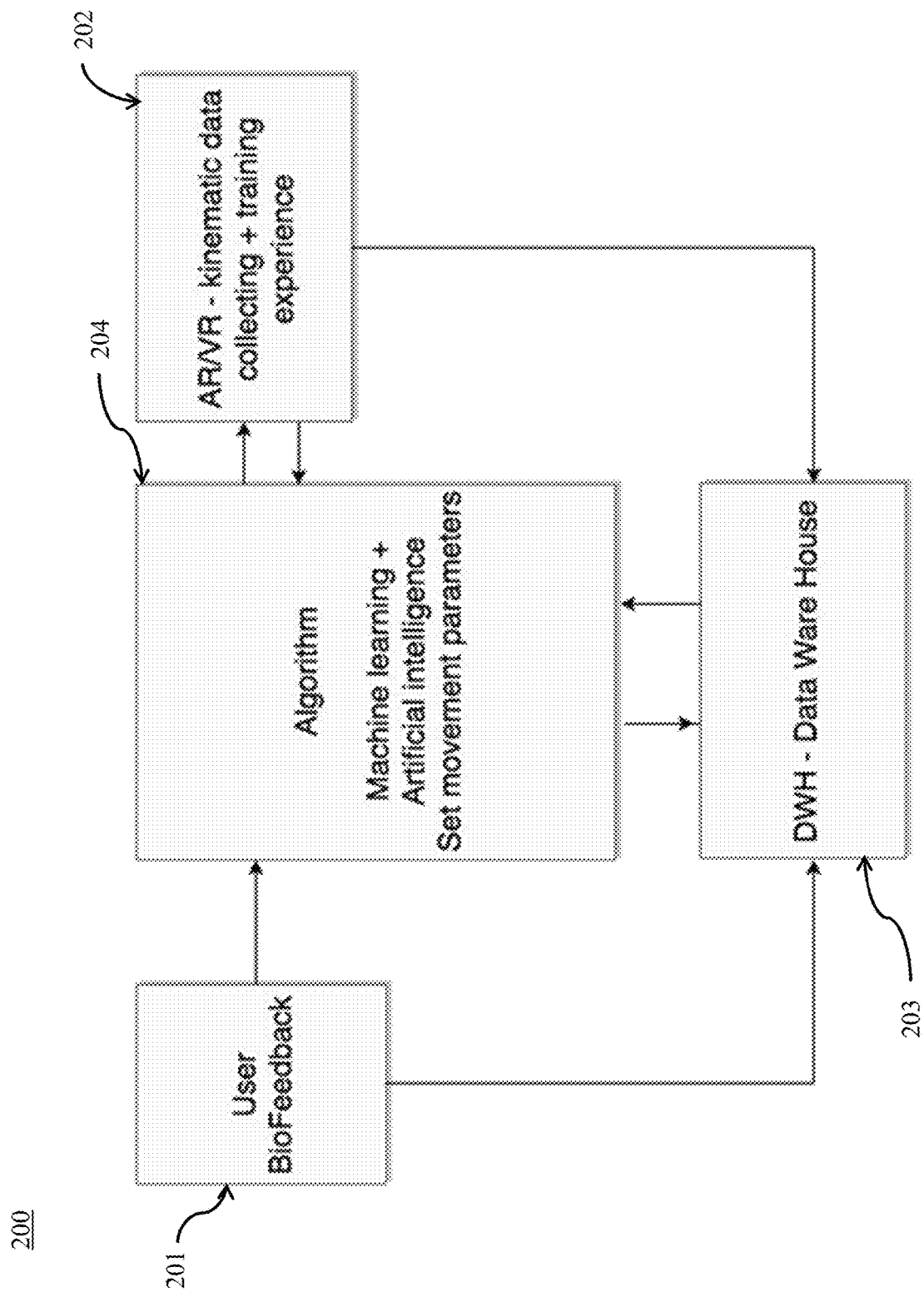
FIG. 2 illustrates a system for adjusting training protocols according to biofeedback according to embodiments of the present disclosure.

Referring to FIG. 2, a system for adjusting training according to biofeedback is illustrated according to the present disclosure. A patient is connected to one or more biofeedback sensors to generated user biofeedback 201, while using an AR or VR device 202 (such as illustrated in connection with FIG. 1). The VR or AR device gathers kinematic data and provides the training experience to the user.

In various embodiments, sensors connected to the user provide: Heart rate variability (HRV); Electrothermal activity (EDA); Galvanic skin response (GSR); Electroencephalography (EEG); Electromyography (EMG); Eye tracking; Electrooculography (EOG); Patient's range of motion (ROM); Patient's velocity performance; Patient's acceleration performance; or Patient's smoothness performance.

Data collected from biofeedback sensors 201 and from AR or VR device 202 are stored in datastore 203. Data are provided from sensors 201, AR or VR device 202, and datastore 203 to machine learning system 204. By receiving biofeedback live from training, learning system 204 provides high level analysis that provides adjustment and adaptation of the training to the patient during the training itself, through changes in the training parameters according to the biofeedback given.

In some embodiments, a feature vector is provided to the learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

In general, the user biofeedback indicators are provided to the machine learning system. Data are aggregated from the different sensors (e.g., biofeedback sensors, VR/AR sensors, or deep cam) and together with insights from past collected data, the learning system gives an output in the form of the next indicated movement in the training session.

For example, if a physical therapy training is too difficult for a patient, making him perform movements that are not appropriate to his needs and abilities or put him at risk of injury, the difficulty will be recognized by the learning system. The learning system may then direct changes in training parameters to make the training suitable to the patient's needs.

Likewise, if a training is too easy for a patient, the learning system may recognize that the user is achieving training goals easily and adapt training parameters to achieve a more efficient training experience.

It will be appreciated that the examples provided herein are applicable to a variety of training experience in AR/VR using biofeedback, such as coordination training and psychology training. Learning systems are provided herein are able to recognize the level of adaptation of the training to the patient, and make immediate changes to better suit training for an individual patient.

In an exemplary embodiment, a user undergoes coordination training. A user is presented with one or more tasks in the virtual or augmented environment, such as grasping or tracking virtual objects, or responding quickly to visual stimuli. As a user performs these tasks, kinematic and biometric data are collected. The difficulty of the tasks may be scaled by the learning system based on the user's performance on the training tasks as well as based on the biometric feedback. For example, a virtual object may move faster, making a coordination task more challenging.

In another exemplary embodiment, a user undergoes exposure therapy. In exposure therapy, a user is exposed to a feared object or context without any danger, in order to overcome their anxiety and/or distress. A feared object or context is presented to a user in the virtual environment, and biometric data are collected. The intensity and duration of the exposure may be scaled by the learning system based on the biometric feedback. For example, exposure may be shortened as a user's heart rate increases beyond a target level.

In another exemplary embodiment, a user undergoes cognitive training. A user is presented with a task in the virtual environment that requires memory, processing speed, or problem-solving skills. For example, a puzzle or maze may be presented. The user's performance on the task is monitored, and the difficulty may be scaled by the learning system based on performance and biometric feedback. For example, heart rate may be considered a proxy for frustration, and difficulty may be scaled back as user frustration increases in order to maintain a productive difficulty level for the individual user.

Figure 3:
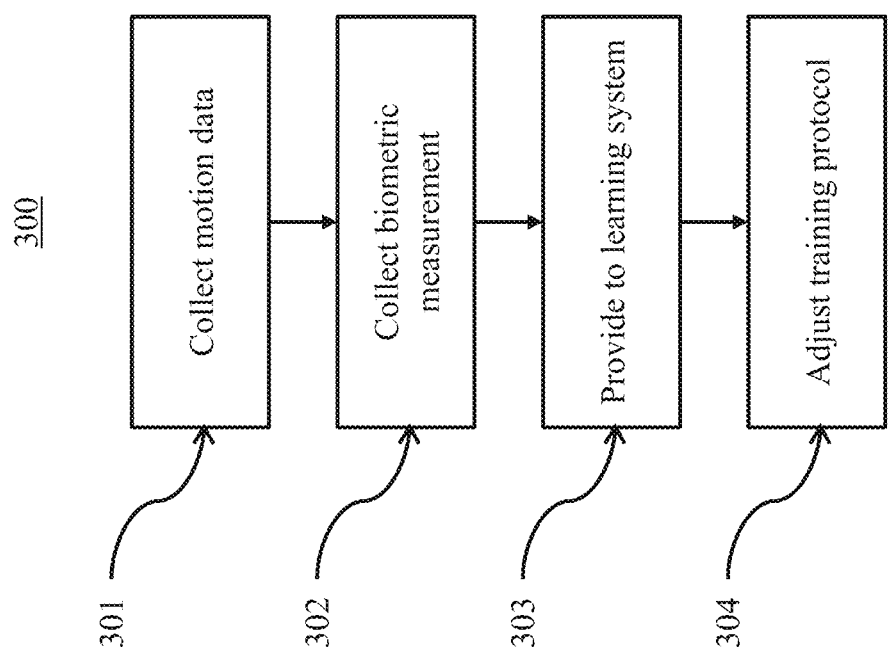
FIG. 3 illustrates a method of adjusting training protocols according to biofeedback according to embodiments of the present disclosure.

Referring to FIG. 3, a method of adjusting training in virtual reality (VR) or augmented reality (AR) environments based on biofeedback is illustrated according to embodiments of the present disclosure. At 301, motion data is collected for a user while the user performs a training protocol. At 302, one or more biometric measurement is collected for the user while the user performs the training protocol. At 303, the motion data and the biometric measurement are provided to a learning system. At 304, one or more adjustments is applied to the training protocol. The one or more adjustments is provided by the learning system based on the motion data and the biometric measurement.

Figure 4:
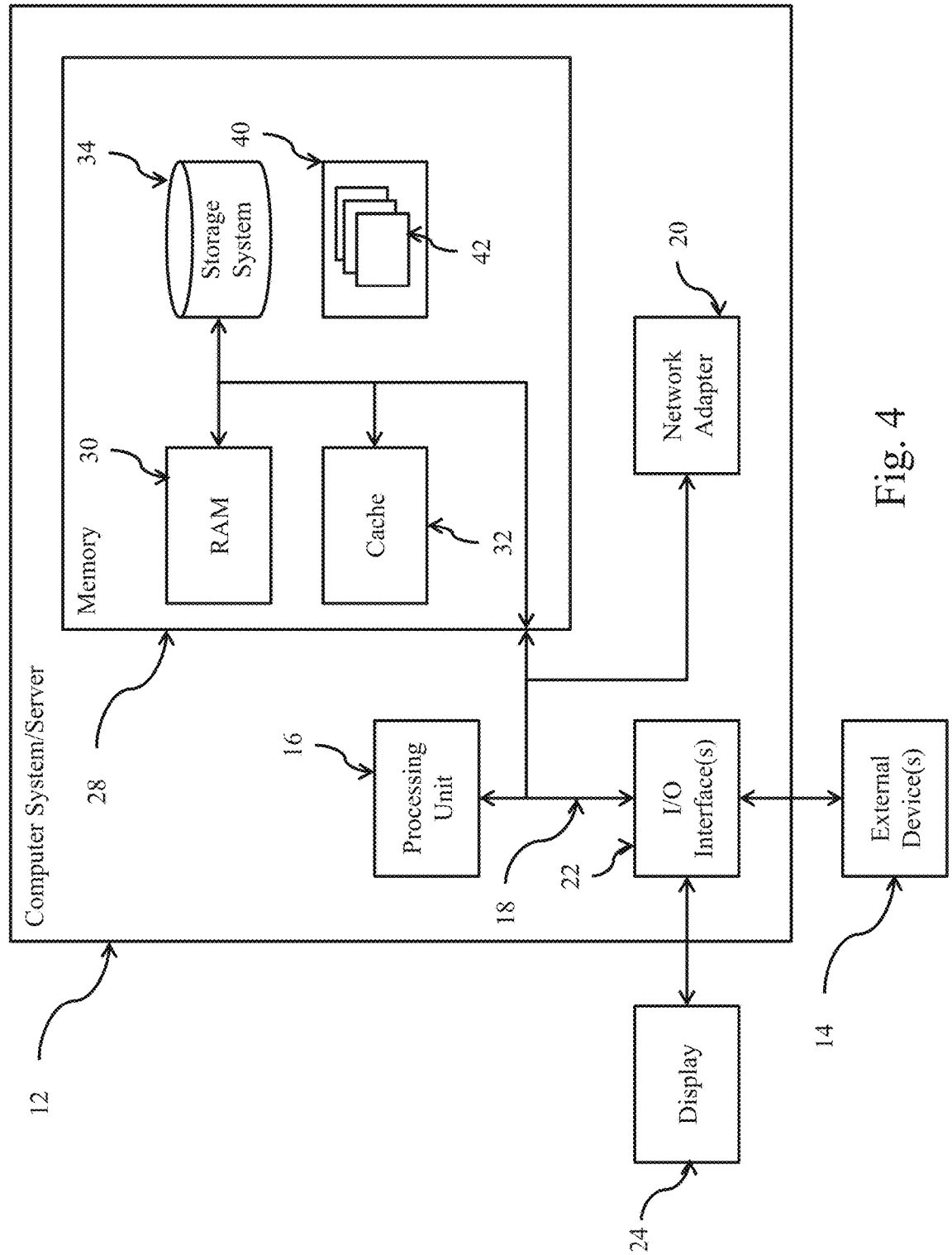
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
providing a virtual environment to a user;
collecting motion data for the user while the user performs a training protocol;
collecting a biometric measurement for the user while the user performs the training protocol;
providing the motion data and the biometric measurement to a learning system at a remote server;
determining an adjustment at the remote server based on the motion data and the biometric measurement;
applying the adjustment to the training protocol, the adjustment being provided by the learning system.

2. The method of claim 1, wherein the biometric measurement is selected from the group comprising: heart rate, blood pressure, breathing rate, electrical activity of the muscles, electrical activity of the brain, pupil dilation, and perspiration.

3. The method of claim 1, further comprising receiving the training protocol from a healthcare record server.

4. The method of claim 3, wherein the healthcare record server comprises a database for storing electronic health records.

5. The method of claim 1, wherein receiving the training protocol comprises accessing an electronic health record of the user in the database to retrieve one or more parameters related to the training protocol.

6. The method of claim 1, further comprising:
determining whether the biometric measurement is above a threshold;
when the biometric measurement is above the threshold, determining an additional adjustment to the training protocol; and
applying the additional adjustment until the biometric measurement is below the threshold.

7. The method of claim 6, further comprising:
determining whether the biometric measurement is below a bottom threshold;
when the biometric measurement is below the bottom threshold, determining an additional adjustment to the training protocol; and
applying the additional adjustment until the biometric measurement is above the bottom threshold.

8. A system comprising:
a virtual or augmented reality display adapted to display a virtual environment to a user;
a biometric sensor coupled to the user;
a computing node comprising a computer readable storage medium having program instructions embodied therewith, the program instructions executable by a processor of the computing node to cause the processor to perform a method comprising:
providing the virtual environment to the user;
collecting motion data from the virtual reality display for the user while the user performs a training protocol;
collecting a biometric measurement from the biometric sensor for the user while the user performs the training protocol;
providing the motion data and the biometric measurement to a learning system at a remote server;
determining an adjustment at the remote server based on the motion data and the biometric measurement;
applying the adjustment to the training protocol, the adjustments being provided by the learning system.

9. The system of claim 8, wherein the biometric measurement is selected from the group comprising: heart rate, blood pressure, breathing rate, electrical activity of the muscles, electrical activity of the brain, pupil dilation, and perspiration.

10. The system of claim 8, further comprising receiving the training protocol from a healthcare record server comprising a database for storing electronic health records.

11. The system of claim 8, wherein receiving the training protocol comprises accessing an electronic health record of the user in the database to retrieve one or more parameters related to the training protocol.

12. The system of claim 8, further comprising:
determining whether the biometric measurement is above a threshold;
when the biometric measurement is above the threshold, determining an additional adjustment to the training protocol; and
applying the additional adjustment until the biometric measurement is below the threshold.

13. The system of claim 12, further comprising:
determining whether the biometric measurement is below a bottom threshold;
when the biometric measurement is below the bottom threshold, determining an additional adjustment to the training protocol; and
applying the additional adjustment until the biometric measurement is above the bottom threshold.

14. A computer program product for adjusting training protocols based on biofeedback, the computer program product comprising a computer readable storage medium having program instructions embodied therewith, the program instructions executable by a processor to cause the processor to perform a method comprising:
providing a virtual environment to a user;
collecting motion data for the user while the user performs a training protocol;
collecting a biometric measurement for the user while the user performs the training protocol;
providing the motion data and the biometric measurement to a learning system at a remote server;
determining an adjustment at the remote server based on the motion data and the biometric measurement;
applying the adjustment to the training protocol, the adjustment being provided by the learning system.

15. The computer program product of claim 14, wherein the biometric measurement is selected from the group comprising: heart rate, blood pressure, breathing rate, electrical activity of the muscles, electrical activity of the brain, pupil dilation, and perspiration.

16. The computer program product of claim 14, further comprising receiving the training protocol from a healthcare record server.

17. The computer program product of claim 16, wherein the healthcare record server comprises a database for storing electronic health records.

18. The computer program product of claim 14, wherein receiving the training protocol comprises accessing an electronic health record of the user in the database to retrieve one or more parameters related to the training protocol.

19. The computer program product of claim 14, further comprising:
determining whether the biometric measurement is above a threshold;
when the biometric measurement is above the threshold, determining an additional adjustment to the training protocol; and
applying the additional adjustment until the biometric measurement is below the threshold.

20. The computer program product of claim 14, further comprising;
determining whether the biometric measurement is below a bottom threshold;
when the biometric measurement is below the bottom threshold, determining an additional adjustment to the training protocol; and
applying the additional adjustment until the biometric measurement is above the bottom threshold.

* * * * *